Figure 1:
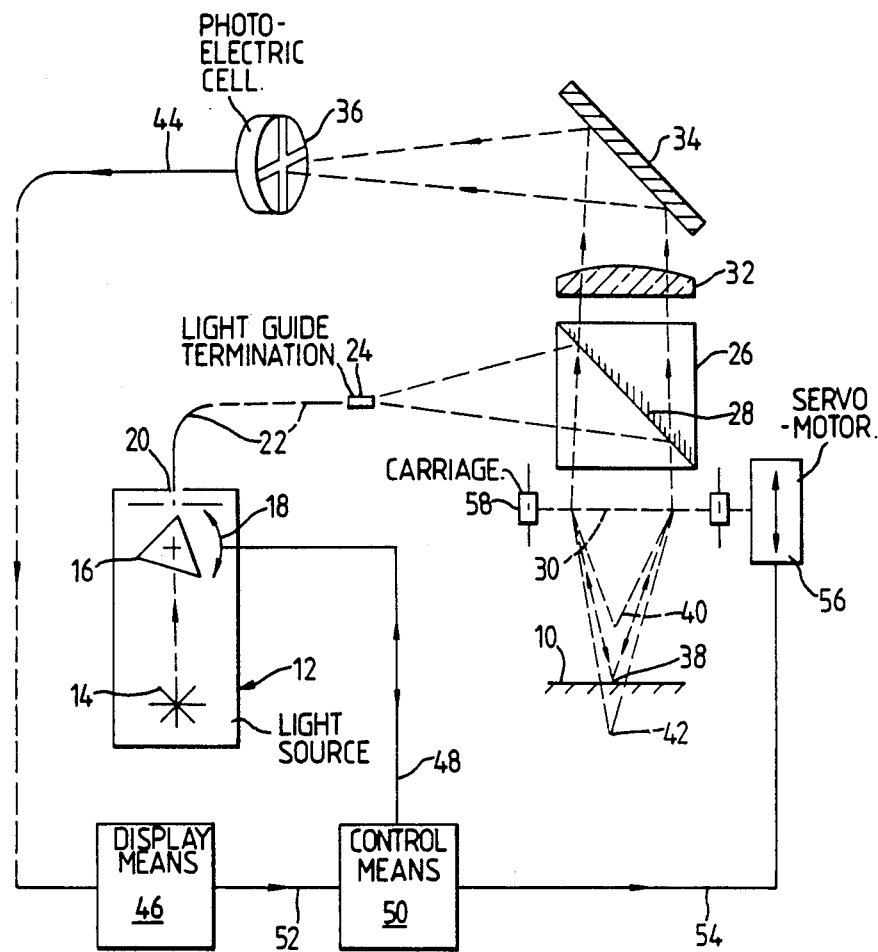

United States Patent [19]

Hutley

[11] Patent Number: 4,600,831
[45] Date of Patent: Jul. 15, 1986

[54] APPARATUS TO FOCUS LIGHT ON A SURFACE BASED ON COLOR

[75] Inventor: Michael C. Hutley, Teddington, England

[73] Assignee: The Secretary of State for Defence in Her Britannic Majesty's Government of the United Kingdom of Great Britain and Northern Ireland, London, England

[21] Appl. No.: 553,956

[22] Filed: Nov. 21, 1983

[30] Foreign Application Priority Data

Dec. 7, 1982 [GB] United Kingdom ............... 8234910

[51] Int. Cl.⁴ .................... G02B 27/40; G03B 3/00
[52] U.S. Cl. .................................. 250/201; 250/226
[58] Field of Search ............... 250/201, 201 AF, 204, 250/226, 201 DF; 354/402, 403, 406, 408, 409; 356/1, 4, 5; 369/44–46

[56] References Cited

U.S. PATENT DOCUMENTS 4,511,232 4/1985 Yamada .................. 354/403

FOREIGN PATENT DOCUMENTS 1582844 1/1981 United Kingdom .
2077421 12/1981 United Kingdom ............... 250/226
2090437 7/1982 United Kingdom .

Primary Examiner—Edward P. Westin
Attorney, Agent, or Firm—William R. Hinds

[57] ABSTRACT

Apparatus to focus light onto a given surface, having a light focusing device which has appreciable chromatic aberration; a variable wavelength light source, supplying light through the focusing device to the given surface; a focus detecting device to receive light from the source reflected from the given surface; and control and indicating devices responsive to the wavelength of the light source and to the focus detecting device to vary the wavelength of the light from the light source to maintain the light in focus on the given surface.

8 Claims, 3 Drawing Figures

APPARATUS TO FOCUS LIGHT ON A SURFACE BASED ON COLOR

This invention relates to apparatus to focus light onto a given surface.

The need is frequently encountered for focusing light from an optical device onto a given surface. Situations in which, by way of example, this is required are non-contacting optical probes or gauges, and readers for video discs. Conventional means exist for determining when light reaches a surface in focus, and for providing signals when there is a departure from focus and to indicate in which sense the optical device and surface must be relatively moved in order to gain or restore focus. Such signals are applied to a servo control system which effects the required focusing by moving a part of the optical device. This may be, for example, a microscope objective of conventional kind, which to be of good enought optical quality may have a mass so large that speed of response of the servo control system may be inconveniently limited.

The present invention provides apparatus in which a focusing optical means need incorporate no movable part at all; speed of response of the servo control system can therefore be improved. Moreover, the light focusing means can be cheap to produce; while its optical quality can still be wholly adequate for the majority of purposes.

According to the invention, apparatus to focus light onto a given surface has a light focusing means which has appreciable chromatic aberration; a variable wavelength light source supplying light through said focusing means, in use, to a said given surface; focus detecting means to receive, in use, light from the source reflected from said given surface; and control and indicating means responsive to the wave-length of the light source and to the focus detecting means to vary the wavelength of the light from the light source to maintain said light in focus on said given surface.

Optionally the apparatus may be arranged so that focus is maintained on said given surface, for a given wavelength of light, by varying the distance of the light focusing means from the given surface.

Preferably the light focusing means is a zone plate. The wavelength of the light from the light source may be varied by an interference filter wedge selecting a required waveband from white light. Alternatively the wavelength of the light from the source may be varied by a monochromator selecting a required waveband from white light. In another embodiment the wavelength of light from the light source is varied by varying the temperature of a semi conductor laser.

Optionally the light is conducted from the light source to the light focusing means through an optical fibre light guide.

Figure 2:
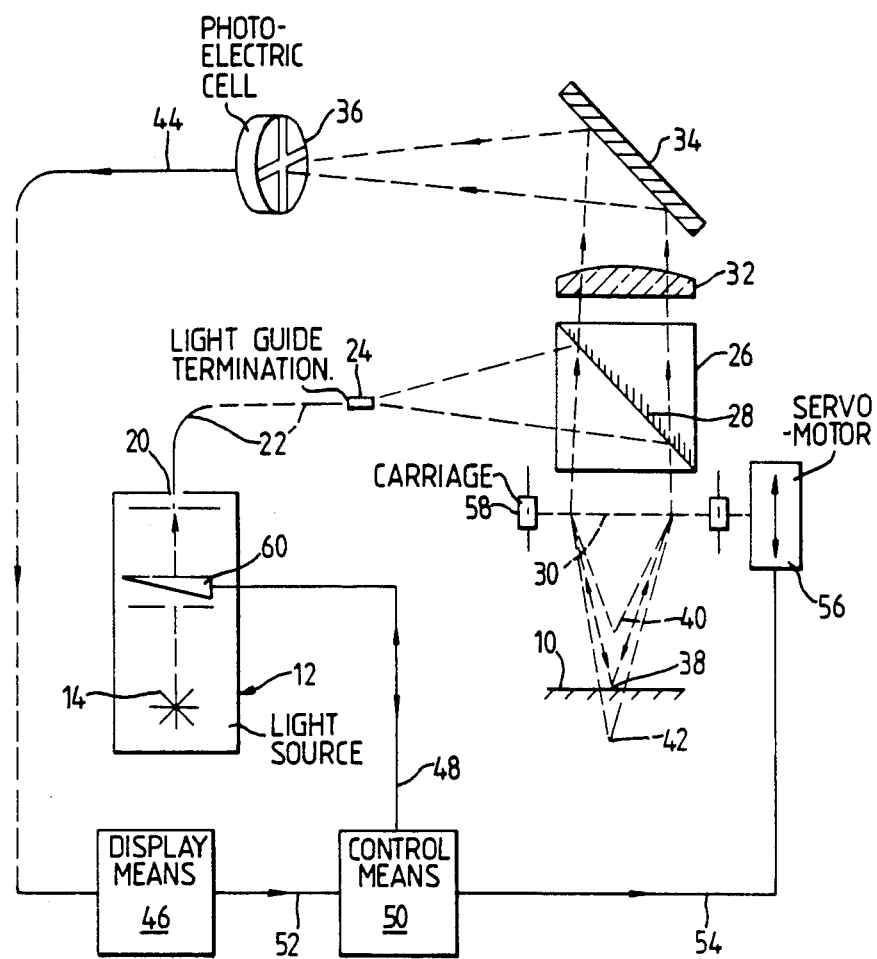
Figure 3:
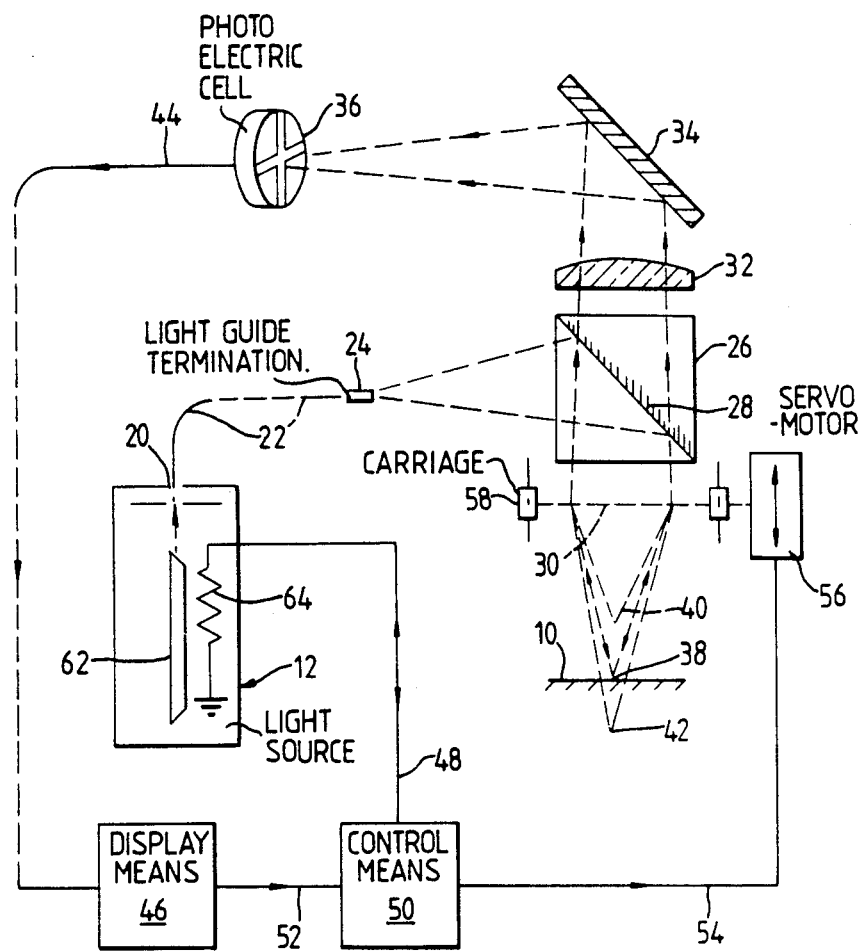

The invention will be further described, by way of example, with reference to the accompanying drawing in which:

FIG. 1 is a diagrammatic illustration of apparatus to focus light onto a given surface FIG. 2 is similar to FIG. 1 but indicates diagrammatically an alternative variable colour light source FIG. 3 illustrates diagrammatically a further alternative variable colour light source.

The surface onto which light is to be focused as indicated (FIG. 1) by 10. This may be, for example, the surface of a video disc. A variable wavelength light source is indicated generally at 12. White light is generated by a lamp 14. Light in a narrow band of wavelengths is selected by a monochromator 16. The monochromator is here indicated as comprising a prism. The wavelength is varied by monochromator adjusting means illustrated diagrammatically by the arrow 18. The light of selected wavelength leaves the light source through an aperture 20 and is conducted, in this example, through a single filament optical fibre light guide 22. Light leaves the guide at a termination 24, and passes into a beam splitter cube 26. At a partially reflecting surface 28 inside the cube, light is directed to a light focusing means 30, which in this embodiment is a zone plate. The zone plate converges the light onto the surface 10 and into an area which is smaller in accordance with the degree to which the light is focused. Light reflected from the surface 10 passes back through the zone plate, and a proportion of the reflected light passes through the partially reflecting surface 28, through a cylindrical lens 32, and via a plane mirror 34 to a quadrant photo electric cell 36. The cylindrical mirror and quadrant photo electric cell in combination are in themselves a conventional means for detecting the goodness of focusing. The quadrant photo electric cell has four outputs, and the relative magnitudes of the outputs can be used as an indication of whether the light onto surface 10 from zone plate 30 reaches a focus onthe surface at 38, above the surface at 40 or below the surface at 42. The outputs from 36 are taken through leads 44 to amplifier and display means 46 where the degree of focus of the light on surface 10 can be indicated.

The zone plate 30 has marked chromatic aberration, and will bring green light into a focus at, say, a position 38, red light at 40 and blue light at 42. Thus a signal 48 indicative of the adjustment of the monochromator (and hence of the colour of light selected) may be combined in a control and indicating means 50 with signals 52 from the focus detecting means 36, 46 to provide an indication of the distance between the zone plate 30 and the surface 10. The monochromator prism may be rotated until the focus detecting means indicates precise focus; that is when the selected wavelength (colour) is such that the light from the zone plate converges substantially on the point 38. An initial calibration enables the monochromator adjusting means to be scaled in terms of distance, say in micrometers, between zone plate and surface, the zone plate itself being the datum. If focusing only is required, the control means 50 may be arranged to actuate, through adjusting means 18, rotation of the monochromator prism in such a sense that the output wavelength changes tending to bring light to focus at 38.

It will be appreciated from the foregoing that the invention provides the advantage that the light focusing means, ie the zone plate 30, does not have to be moved in relation to the surface 10. Thus the only appreciable lag in the system is that which may be associated with the adjustment of the monochromator 12, or other means for selecting the required wavelength of light.

In some application of the invention, it may be convenient to vary the distance between zone plate 30 as datum and surface 10 in order to maintain focus. The monochromator 16 may then be set by the adjusting means 18 for a normal distance at which light will be in focus at 38, and a constant signal 48 will be fed into the control and indicating means 50. If the distance varies from the normal the focus detecting means will feed a signal 52 which will be dependent (in polarity, magnitude or other manner) on whether the surface has moved nearer to position 40 or to position 42. The two signals 48 and 52 are combined in the control and indicating means 50 to produce a control signal 54 which actuates a servo motor 56 to drive the zone plate 30, supported on a light-weight carriage 58, in such a sense as to restore coincidence between the surface 10 and the light focus 38.

A zone plate with its mount (carriage 58) may be made to have a mass of the order of one or two gramme. This compares favourably with such focusing means as a conventional microscope objective, mentioned above, which may have a mass of as much as 100 gramme. The smaller mass implies quicker servo response times.

In the embodiment described above, the monochromator is of the rotatable prism kind. One alternative is an interference filter wedge, indicated diagrammatically at 60 in FIG. 2, which selects a required narrow waveband from white light. Another alternative is a laser in the form of a semi-conductor diode, indicated diagrammatically at 62 in FIG. 3, the wavelength of emitted light being dependent on the temperature of the diode. The apparatus then includes means, such as a thermostatically controlled oven, indicated at 64, to maintain the temperature at a predeterminable constant value.

A further application of the invention is in endoscopes. A zone plate is arranged to form at least part of the lens system at the distal end (that is the opposite end from the eyepiece) of an endoscope, intended for insertion into a body cavity. A change in wavelength of the light input to the endoscope cause the zone plate to focus to a different distance from the end of the endoscope. This provides the effect of a zoom lens system without moving parts and with remote control through a monochromator. This facility is of particular advantage in an endoscope employing a coherent optical fibre to transmit light to the eyepiece from the object under examination.

I claim:

1. Apparatus to focus light onto a given surface having a light focusing means which has appreciable chromatic aberration; a variable wavelength light source supplying light through said focusing means to said given surface; focus detecting means to receive light from the source reflected from said given surface; and control and indicating means responsive to the wavelength of the light source and to the focus detecting means to vary the wavelength of the light from the light source to maintain said light in focus on said given surface.

2. Apparatus according to claim 1 arranged so that focus is maintained on said given surface, for a given wavelength of light, by varying the distance of the light focusing means from the given surface.

3. Apparatus according to claim 1 in which the light focusing means is a zone plate.

4. Apparatus according to claim 1 in which the wavelength of the light from the light source is varied by an interference filter wedge selecting a desired waveband from white light.

5. Apparatus according to claim 1 in which the wavelength of the light from the source is varied by a monochromator selecting a desired waveband from white light.

6. Apparatus accordiong to claim 1 in which the wavelength of the light from the light source is varied by varying the temperature of a semi-conductor laser, said laser being the light source.

7. Apparatus according to claim 1 in which the light is conducted from the light source to the light focusing means through an optical fibre light guide.

8. Apparatus according to claim 1, in combination with an endoscope, and so arranged that the light focusing means which has appreciable chromatic aberration is in the distal end of the endoscope, whereby light can be focused to a variable distance from the distal end of said endoscope.

* * * * *